(12) United States Patent
Tang et al.

(10) Patent No.: US 9,175,079 B2
(45) Date of Patent: Nov. 3, 2015

(54) DEPLETION OF TERATOMA-FORMING PLURIPOTENT STEM CELLS

(75) Inventors: Chad Tang, East Palo Alto, CA (US); Irving L. Weissman, Stanford, CA (US); Micha Drukker, Stanford, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 295 days.

(21) Appl. No.: 13/575,511

(22) PCT Filed: Jan. 28, 2011

(86) PCT No.: PCT/US2011/022919
§ 371 (c)(1),
(2), (4) Date: Oct. 17, 2012

(87) PCT Pub. No.: WO2011/094538
PCT Pub. Date: Aug. 4, 2011

(65) Prior Publication Data
US 2013/0028909 A1   Jan. 31, 2013

Related U.S. Application Data

(60) Provisional application No. 61/299,846, filed on Jan. 29, 2010.

(51) Int. Cl.
*A61K 38/00* (2006.01)
*C07K 16/00* (2006.01)
*C07K 16/28* (2006.01)
*C12N 5/00* (2006.01)

(52) U.S. Cl.
CPC .............. *C07K 16/28* (2013.01); *C12N 5/0081* (2013.01)

(58) Field of Classification Search
None
See application file for complete search history.

(56) References Cited

U.S. PATENT DOCUMENTS

| 4,545,985 | A | 10/1985 | Pastan et al. |
| 2007/0212356 | A1 | 9/2007 | Chen et al. |
| 2009/0263896 | A1 | 10/2009 | Kelly et al. |
| 2010/0144039 | A1* | 6/2010 | Chambers et al. ............ 435/455 |
| 2010/0145032 | A1* | 6/2010 | Laine et al. .................. 530/395 |
| 2011/0312091 | A1* | 12/2011 | Zhao et al. ................... 435/368 |

FOREIGN PATENT DOCUMENTS

WO    WO 2008087258    *    7/2008

OTHER PUBLICATIONS

Drusenheimer; et al. "Putative human male germ cells from bone marrow stem cells", Soc Reprod Fetil Suppl (2007), 63:69-76.

Fouladi-Nashta; et al. "Characterization of the uterine phenotype during the peri-implantation period for LIF-null, MF1 strain mice", Dev Biol (May 2005), 281(1):1-21.

Fredman; et al."A monoclonal antibody that precipitates the glycoprotein receptor for epidermal growth factor is directed against the human blood group H type 1 antigen", J Biol Chem (Sep. 1983), 258(18):11206-11210.

* cited by examiner

*Primary Examiner* — Michail Belyavskyi
(74) *Attorney, Agent, or Firm* — Bozicevic, Field & Francis LLP; Pamela J. Sherwood

(57) ABSTRACT

Compositions and methods are provided for depletion of pluripotent cells. In one embodiment of the invention, methods are provided for depletion of pluripotent cells from a mixed population of differentiated cells and stem cells, to provide a population of cells substantially free of pluripotent stem cells. Monoclonal antibodies useful in depletion and in identification of pluripotent stem cells are also provided.

8 Claims, 4 Drawing Sheets

DEPLETION OF TERATOMA-FORMING PLURIPOTENT STEM CELLS

GOVERNMENT RIGHTS

This invention was made with Government support under grant no. RC1-00354-1 awarded by the California Institute of Regenerative Medicine. The Government has certain rights in this invention.

BACKGROUND OF THE INVENTION

Regenerative medicine is the process of creating living, functional tissues to repair or replace tissue or organ function lost due to age, disease, damage, or congenital defects. This field holds the promise of regenerating damaged tissues and organs in the body by introducing outside cells, tissue, or even whole organs to integrate and become a part of tissues or replace whole organ. Importantly, regenerative medicine has the potential to solve the problem of the shortage of organs available for donation compared to the number of patients that require life-saving organ transplantation.

One key to the success of regenerative medicine strategies has been the ability to isolate and generate stem cells, including pluripotent stem cells. In one aspect, pluripotent stem cells can be differentiated into a necessary cell type, where the mature cells are used to replace tissue that is damaged by disease or injury. This type of treatment could be used to replace neurons damaged by spinal cord injury, stroke, Alzheimer's disease, Parkinson's disease, or other neurological problems. Cells grown to produce insulin could treat people with diabetes and heart muscle cells could repair damage after a heart attack. This list could conceivably include any tissue that is injured or diseased.

The generation of pluripotent stem cells that are genetically identical to an individual provides unique opportunities for basic research and for potential immunologically-compatible novel cell-based therapies. Methods to reprogram primate somatic cells to a pluripotent state include differentiated somatic cell nuclear transfer, differentiated somatic cell fusion with pluripotent stem cells, and direct reprogramming to produce induced pluripotent stem cells (iPS cells) (Takahashi K, et al. (2007) Cell 131:861-872; Park I H, et al. (2008) Nature 451:141-146; Yu J, et al. (2007) Science 318:1917-1920; Kim D, et al. (2009) Cell Stem Cell 4:472-476; Soldner F, et al. (2009) Cell. 136:964-977; Huangfu D, et al. (2008) Nature Biotechnology 26:1269-1275; Li W, et al. (2009) Cell Stem Cell 4:16-19).

A significant first hurdle in stem cell-based therapy is the differentiation of pluripotent cells into a desired tissue type. Such methods currently rely on the step-wise introduction of factors and conditions to guide the cells down a developmental pathway, resulting eventually in a mature or committed progenitor cell that can transplanted into a patient.

The promise of pluripotent stem cells is that they can form any type of cell in the body. The trouble is that when implanted into an animal they do just that, forming all tissue types in the form of teratomas. These teratomas are one reason why it is necessary to mature the embryonic stem cells into highly purified adult cell types before they are considered appropriate for implanting into humans. The mature cells are restricted to their one identity and don't appear to revert to a teratoma-forming cell. However, even when researchers have learned to mature cells into a single cell type, getting those cells pure enough to eliminate the risk of remaining immature cells forming teratomas has been extremely difficult.

Clinical applications may utilize billions of cells injected into large numbers of clinically diverse patients, many of whom will be expected to live out their whole lifetimes (i.e. pediatric patients). As such it is important to thoroughly deplete residual pluripotent stem cells.

A caveat to the clinical application of ES/iPS derived derivatives is that the in vivo implantation of even trace amounts of undifferentiated cells may result in uncontrolled teratomas. The present invention addresses this issue.

SUMMARY OF THE INVENTION

Compositions and methods are provided for depletion of pluripotent cells. In one embodiment of the invention, methods are provided for depletion of pluripotent cells from a mixed population of differentiated cells and stem cells, to provide a population of cells substantially free of pluripotent stem cells. Monoclonal antibodies useful in depletion and in identification of pluripotent stem cells are also provided.

Methods of depletion include contacting a mixed population of cells with a cocktail of antibodies that specifically bind to a plurality of pluripotent markers, usually at least 2 markers, and in some embodiments 3, 4, 5, 6 or more markers. Markers of interest include the marker panel CD9, CD30, CD50, CD90, CD200 and H type-1 antigen. Alternatively an antibody specific for H type-1 antigen is used for depletion, optionally in combination with one or more of the marker panel above. Usually a monoclonal antibody that binds to the epitope recognized by 8e11 is included in the cocktail of depleting antibodies. In some methods the cocktail of antibodies consists of antibodies specific for this marker panel, which is shown to provide for effective depletion of pluripotent cells from a population.

In other embodiments the antibodies and/or antibody cocktails of the invention are used to select for fully reprogrammed induced pluripotent stem cells, where expression of one or more of the markers is indicative of a cell that is reprogrammed to pluripotency or is destined to be fully reprogrammed to pluripotency.

An antibody of particular interest specifically binds the H type-1 marker, which is shown to be present at high levels on pluripotent cells. The antigen includes the carbohydrate of the structure Fucα1-2Galβ1-3GlcNAcβ. In some embodiments an anti-H type-1 antibody binds to the cognate epitope of the monoclonal antibody 8e11. In some embodiments the antibody is the 8e11 monoclonal antibody or the binding fragment therefrom. For example an antibody may be a full length antibody, e.g. having a human immunoglobulin constant region of any isotype, e.g. IgG1, IgG2a, IgG2b, IgG3, IgG4, IgA, etc. The antibody may be utilized as an Fab fragment, as a chimeric antibody, e.g. comprising a human Fc region, as a humanized antibody, as a bispecific antibody, etc. Furthermore, the antibody may be labeled with a detectable label, immobilized on a solid phase and/or conjugated with a heterologous compound. Embodiments of the invention include isolated antibodies and derivatives and fragments thereof, pharmaceutical formulations comprising one or more of monoclonal antibodies; and cell lines that produce these monoclonal antibodies.

In some embodiments of the invention, the mixed population of cells is provided in vitro, e.g. in a cell culture. In such cultures the pluripotent cells may be iPS cells, embryonic stem cells, embryonic germ cells, and the like. The cultures may involve differentiation of the pluripotent cells, where the methods of the invention are useful in depleting residual cells that are not differentiated. In vitro methods of depletion may utilize cell sorting technology, e.g. FACS, MACS, affinity chromatography, etc., where labeled antibodies are added to the mixed cell population, and the cells that bind to the antibodies are separated from the unbound cells.

In other embodiments the mixed population of cells is present in vivo. In such embodiments the antibodies may be administered in combination with a population of cells suspected of comprising pluripotent cells, where the population may be a sorted or differentiated population of cells being administered for therapeutic purposes. Alternatively antibodies may be administered following administration of a potentially mixed cell population, where pluripotent stem cells have a potential to be present in the population. Of interest is the administration of an anti-H type-1 antibody.

In other in vivo embodiments, the antibodies are administered for the treatment of teratomas, where an anti-H type-1 antibody or a cocktail of antibodies specific for a panel of pluripotent markers is administered to a patient for the treatment of a teratoma tumor. In other embodiments the antibodies are utilized to detect teratomas, e.g. teratomas formed as a result of injection of the ES/iPS derived therapeutic product, naturally occurring teratomas, teratocarcinomas, other germ cell tumors, etc. The antibodies may be used in imaging modalities conjugated to labels such as FDG (for PET), to detect soluble teratoma/germ cell tumor derived antigens found in the blood, and the like.

DETAILED DESCRIPTION OF THE INVENTION

Figure 1:
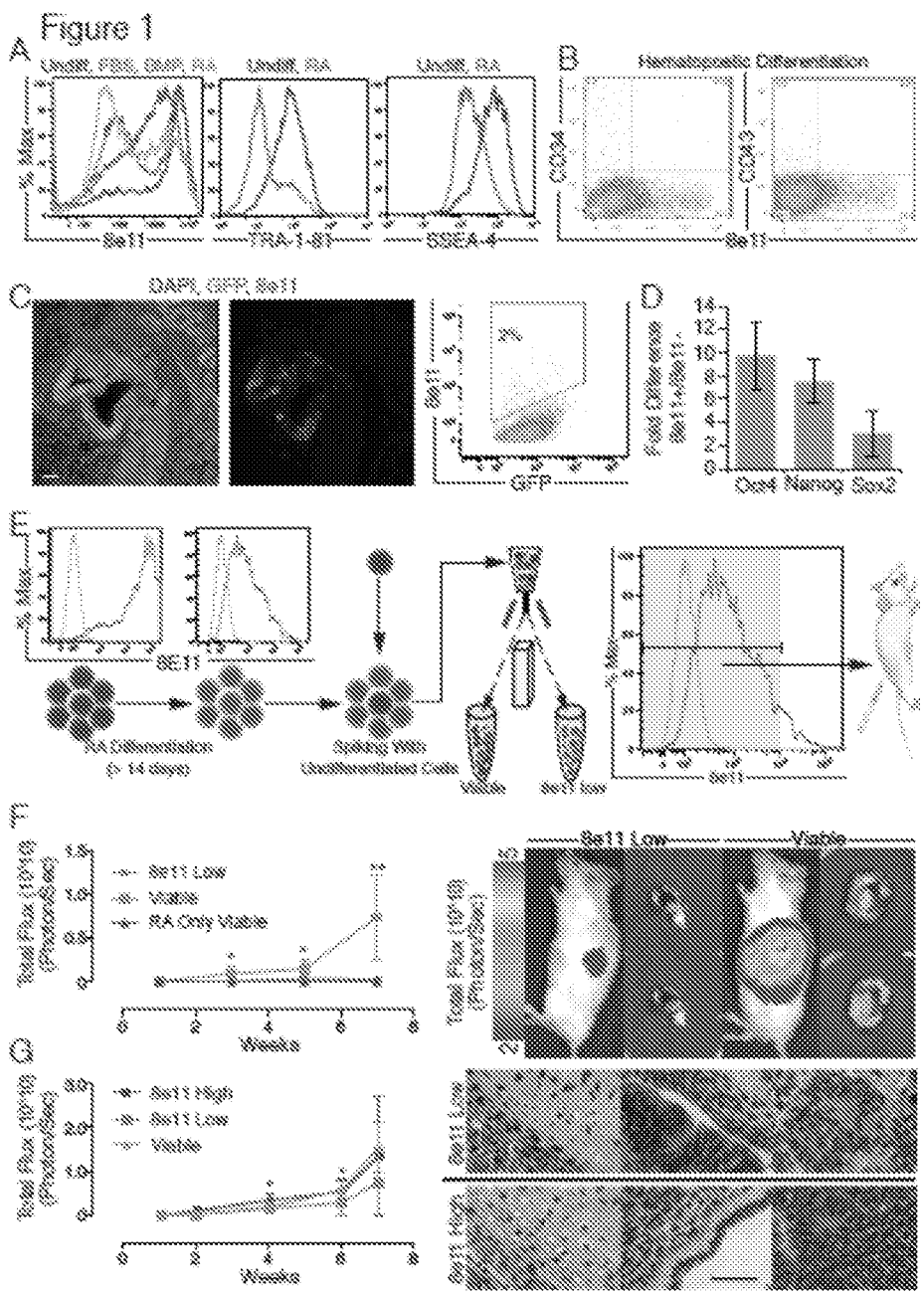
FIG. 1. 8e11 mAb staining of hESCs. (a) Representative FACS plots demonstrating 8e11 binding to undifferentiated hESCs (blue), and decline of signal on differentiated cells treated for 8 days with FBS (orange), RA (grey), and BMP4 (purple). Compared to 8e11, TRA-1-81 and SSEA-4 exhibited lower intensity on undifferentiated hESCs (blue) with a smaller dynamic range during differentiation (red). (b) Mutually exclusive expression of 8e11 and hematopoietic markers CD34 and CD43 on hESCs differentiated towards the hematopoietic lineage. (c) Rare epithelial structures (immunohistochemistry) consisting of ~2% total cells (flow cytometry) were detected by 8e11 in 12 week hESC-derived teratomas. (d) Pluripotency genes OCT4, NANOG, and SOX2 are enriched in 8e11 high versus low populations sorted from hESCs differentiated in RA for 7 days. (e) Schematic illustration of spiking experiments: dissociated 14 day RA differentiated hESCs (red) were spiked with undifferentiated cells (blue) at 100:1. Viable and 8e11 low populations were sorted and injected under the kidney capsules of immunodeficient mice. Inset FACS plots present 8e11 expression and gating. (f) Time series luciferase signal of viability-sorted 14 day RA differentiated hESCs (green), viability-sorted spiked mixtures (blue), and 8e11 low cells sorted from spiked mixtures (red). Right panels are representative luciferase imaging of explanted kidneys. (g) Time series luciferase signal of implants from 3 day RA-treated hESCs sorted for viability (blue), 8e11 high (purple), and 8e11 low (red). Right panels are representative Hematoxylin and Eosin sections of explanted tissues. Scale bar: 100 um, (*) p-value<0.05, and (**) p-value<0.01.

Compositions and methods are provided for depletion of pluripotent cells in vitro or in vivo. Pluripotent cells include iPS cells, embryonic stem cells, teratoma cancer stem cells, germ cell cancers (i.e. teratocarcinomas), etc. In one embodiment of the invention, methods are provided for depletion of pluripotent cells from a mixed population of differentiated cells and stem cells, to provide a population of cells substantially free of pluripotent stem cells. Monoclonal antibodies useful in depletion and in identification of pluripotent stem cells are also provided. Methods of depletion include contacting a mixed population of cells with a cocktail of antibodies that specifically bind to a plurality of pluripotent markers, usually at least 2 markers, and in some embodiments 3, 4, 5, 6 or more markers. Markers of interest include the marker panel CD9, CD30, CD50, CD90, CD200 and H type-1 antigen. Alternatively an antibody specific for H type-1 antigen is used for depletion, optionally in combination with one or more of the marker panel above. In some methods the cocktail of antibodies consists of antibodies specific for this marker panel, which is shown to provide for effective depletion of pluripotent cells from a population.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

By "pluripotency" and pluripotent stem cells it is meant that such cells have the ability to differentiate into all types of cells in an adult organism. The term "induced pluripotent stem cell" encompasses pluripotent cells, that, like embryonic stem (ES) cells, can be cultured over a long period of time while maintaining the ability to differentiate into all types of cells in an organism, but that, unlike ES cells (which are derived from the inner cell mass of blastocysts), are derived from differentiated somatic cells, that is, cells that had a narrower, more defined potential and that in the absence of experimental manipulation could not give rise to all types of cells in the organism. By "having the potential to become iPS cells" it is meant that the differentiated somatic cells can be induced to become, i.e. can be reprogrammed to become, iPS cells. In other words, the somatic cell can be induced to redifferentiate so as to establish cells having the morphological characteristics, growth ability and pluripotency of pluripotent cells. iPS cells have an hESC-like morphology, growing as flat colonies with large nucleo-cytoplasmic ratios, defined borders and prominent nucleoli. In addition, iPS cells express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, pluripotent cells are capable of forming teratomas. In addition, they are capable of forming or contributing to ectoderm, mesoderm, or endoderm tissues in a living organism.

The term "antibody" is used in the broadest sense and specifically covers monoclonal antibodies (including full length monoclonal antibodies), polyclonal antibodies, multi-specific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

As used in this invention, the term "epitope" means any antigenic determinant on an antigen to which the paratope of an antibody binds, particularly H type-1 antigen as recognized by 8e11 monoclonal antibody.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, IgA$_2$. The heavy-chain constant domains that correspond to the different classes of immunoglobulins are called α, β, ε, γ, and μ, respectively. The subunit structures and three-dimensional configurations of different classes of immunoglobulins are well known.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Each mAb is directed against a single determinant on the antigen. In addition to their specificity, the monoclonal antibodies are advantageous in that they can be synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made in an immortalized B cell or hybridoma thereof, or may be made by recombinant DNA methods.

The monoclonal antibodies herein include hybrid and recombinant antibodies produced by splicing a variable (including hypervariable) domain of an anti-H type-1 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 75% by weight of antibody as determined by the Lowry method, and most preferably more than 80%, 90% or 99% by weight, or (2) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

Methods of Depleting Pluripotent Cells

The present invention provides methods of depleting a population of human cells of pluripotent stem cells. The population of cells depleted by the methods described herein are substantially free of pluripotent stem cells. By substantially free of pluripotent cells, it is intended that less than 1 in $10^7$ cells have the properties of a pluripotent cell, as described herein, usually less than 1 in $10^8$, more usually less than 1 in $10^9$, and preferably less than 1 in $10^{10}$.

The methods described herein are based on the observation that (i) H type-1 antigen is expressed at high levels on pluripotent cells; (ii) H type-1 antigen expression decreases with time in all differentiation conditions tested; and (iii) a cocktail of pluripotent markers selected from CD9, CD30, CD50, CD90, CD200 and H type-1 antigen, which may include one or more, including all of the markers, provides for efficient depletion of pluripotent cells.

For in vitro embodiments, the mixed population of cells may include any population suspecting of comprising a mixture of differentiated and pluripotent cells. Of particular interest are cultures of stem cells prepared as therapeutic agents, e.g. cells differentiated into a pathway of interest, where residual stem cells may be present.

Ex vivo and in vitro differentiated cell populations useful as a source of cells may be obtained from any mammalian species, e.g. human, primate, equine, bovine, porcine, canine, feline, etc., particularly human cells. Ex vivo and in vitro differentiated cell populations may include fresh or frozen cells, which may be from a neonate, a juvenile or an adult, and differentiated tissues including skin, muscle, blood, liver, pancreas, lung, intestine, stomach, and other differentiated tissues.

For depletion of pluripotent cells, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The pluripotent cells are depleted from the complex mixture of cells by affinity separation techniques utilizing antibodies, e.g. anti-H type-1 antigen, a cocktail of pluripotent markers, etc. In some embodiments, the subject cells are separated from the complex mixture of cells immediately following dispersion or suspension of the cells. Techniques for affinity separation may include flow cytometry, magnetic separation using magnetic beads coated with an affinity reagent, affinity chromatography, cytotoxic agents joined to an affinity reagent or used in conjunction with an affinity reagent, e.g. complement and cytotoxins, and "panning" with an affinity reagent attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the selected cells.

The affinity reagents may be antibodies, alternatively, specific receptors or ligands may be used; peptide ligands and receptor; effector and receptor molecules, T-cell receptors specific for SSEA3, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art. The affinity reagents specifically bind to a plurality of pluripotent markers, usually at least 2 markers, and in some embodiments 3, 4, 5, 6 or more markers. Markers of interest include the marker panel CD9, CD30, CD50, CD90, CD200 and H type-1 antigen. Alternatively an antibody specific for H type-1 antigen is used for depletion, optionally in combination with one or more of the marker panel above. For example, the monoclonal antibody, 17-206, is commercially available through the company Abcam. This antibody is available in only the ascities formulation and has been reported to bind the H-type 1 glycan.

Conveniently, these antibodies are conjugated with a label for use in separation. Labels include magnetic beads, which allow for direct separation; biotin, which can be removed with avidin or streptavidin bound to a support; fluorochromes, which can be used with a fluorescence activated cell sorter; or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 60 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA or 1-4% goat serum. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, goat serum etc. Cells that express one or a plurality of the pluripotent markers are depleted from the cell population.

The depleted cells, which lack pluripotent stem cells, may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions depleted of pluripotent cells are achieved in this manner. The depleted cell population may be used immediately. Alternatively, the depleted cell population may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cells.

Polypeptides

In one aspect, the present invention is directed to a monoclonal antibody having the epitopic specificity of 8e11, and cell lines which produce such antibodies. The isolation of cell lines producing monoclonal antibodies of the invention can be accomplished using routine screening techniques which permit determination of the elementary reaction pattern of the monoclonal antibody of interest. Thus, if a monoclonal antibody being tested binds to the cognate epitope of 8e11, i.e. cross-blocks, then the monoclonal antibody being tested and the monoclonal antibody produced by the cell lines of the invention are equivalent.

It is also possible to determine, without undue experimentation, if a monoclonal antibody has the same specificity as a monoclonal antibody of the invention by ascertaining whether the former prevents the latter from binding to H type-1 antigen. If the monoclonal antibody being tested competes with the monoclonal antibody of the invention, as shown by a decrease in binding by the monoclonal antibody of the invention, then the two monoclonal antibodies bind to the same, or a closely related, epitope. Still another way to determine whether a monoclonal antibody has the specificity of a monoclonal antibody of the invention is to pre-incubate the monoclonal antibody of the invention with H type-1 antigen with which it is normally reactive, and then add the monoclonal antibody being tested to determine if the monoclonal antibody being tested is inhibited in its ability to bind H type-1 antigen. If the monoclonal antibody being tested is inhibited then, in all likelihood, it has the same, or functionally equivalent, epitopic specificity as the monoclonal antibody of the invention.

In addition to Fabs, smaller antibody fragments and epitope-binding peptides having binding specificity for at least one epitope recognized by 8e11 are also contemplated by the present invention. For example, single chain antibodies can be constructed according to the method of U.S. Pat. No. 4,946,778 to Ladner et al, which is incorporated herein by reference in its entirety. Single chain antibodies comprise the variable regions of the light and heavy chains joined by a flexible linker moiety. Yet smaller is the antibody fragment known as the single domain antibody, which comprises an isolate VH single domain. Techniques for obtaining a single domain antibody with at least some of the binding specificity of the intact antibody from which they are derived are known in the art. For instance, Ward, et al. in "Binding Activities of a Repertoire of Single Immunoglobulin Variable Domains Secreted from *Escheria coli*," Nature 341: 644-646, disclose a method for screening to obtain an antibody heavy chain variable region (H single domain antibody) with sufficient affinity for its target epitope to bind thereto in isolate form.

The monoclonal antibodies of the invention can be used in vitro and in vivo for identification and depletion of pluripotent stem cells, including the treatment of teratomas. The monoclonal antibodies of the invention may be used in vitro in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of pluripotent cells, e.g. teratomas. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bio-luminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

For purposes of the invention, pluripotent stem cells may be detected by the monoclonal antibodies of the invention when present in biological fluids and tissues. Any sample containing a detectable number of pluripotent stem cells can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Therapeutic formulations comprising one or more antibodies of the invention are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary, e.g. to deplete substantially all pluripotent cells from a complex mixture; or to decrease the number of teratoma cells in a patient.

The therapeutic dose may be at least about 0.01 µg/kg body weight, at least about 0.05 µg/kg body weight; at least about 0.1 µg/kg body weight, at least about 0.5 µg/kg body weight, at least about 1 µg/kg body weight, at least about 2.5 µg/kg body weight, at least about 5 µg/kg body weight, and not more than about 100 µg/kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g. i.m., i.p., i.v., and the like.

The antibody need not be, but is optionally formulated with one or more agents currently used to prevent or treat cancer. These are generally used in the same dosages and with administration routes as used hereinbefore or about from 1 to 99% of the heretofore employed dosages.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The formulation herein may also contain more than one active compound as necessary for the particular indication being treated, preferably those with complementary activities that do not adversely affect each other.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

For the prevention or treatment of disease, the appropriate dosage of antibody will depend on the type of disease to be treated, as defined above, the severity and course of the disease, whether the antibody is administered for preventive purposes, previous therapy, the patient's clinical history and response to the antibody, and the discretion of the attending physician. The antibody is suitably administered to the patient at one time or over a series of treatments.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody or cocktail of antibodies. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

We sought to discover a comprehensive surface marker profile expressed by undifferentiated ES/iPS cells. We then sought to show that it is possible to achieve the functional separation of undifferentiated from differentiated cells via fluorescence activated cell sorting (FACS) through application of this panel.

To identify a cell surface markers specific for pluripotent cells, we created a hybridoma library against undifferentiated H9 ES cells via the decoy immunization method. We subsequently sub-cloned each hybridoma to single cell cultures and tested the secreted monoclonal antibodies (mAbs) for binding on undifferentiated ES cells and those differentiated in the presence of retinoic acid (RA) or bone morphogenic protein 4 (BMP).

One mAb in particular (designated 8e11) was of particular interest as it exhibited extremely high fluorescence intensity when used to analyze undifferentiated ES cells in flow cytometry (FIG. 1a). Furthermore, differentiation decreases fluorescence intensity by 2-3 orders of magnitude (FIG. 1a,b), a substantially greater reduction compared with that observed with the known and current "gold standard" markers Tra-1-81 and SSEA4 (FIG. 1d). Finally immunohistochemistry with 8e11 on 12 week old teratomas grown from H9 ES cells in severe combined immunodeficient (SCID) mice noted the appearance or relatively rare epithelial structures which stained for 8e11 (FIG. 1c).

Figure 2:
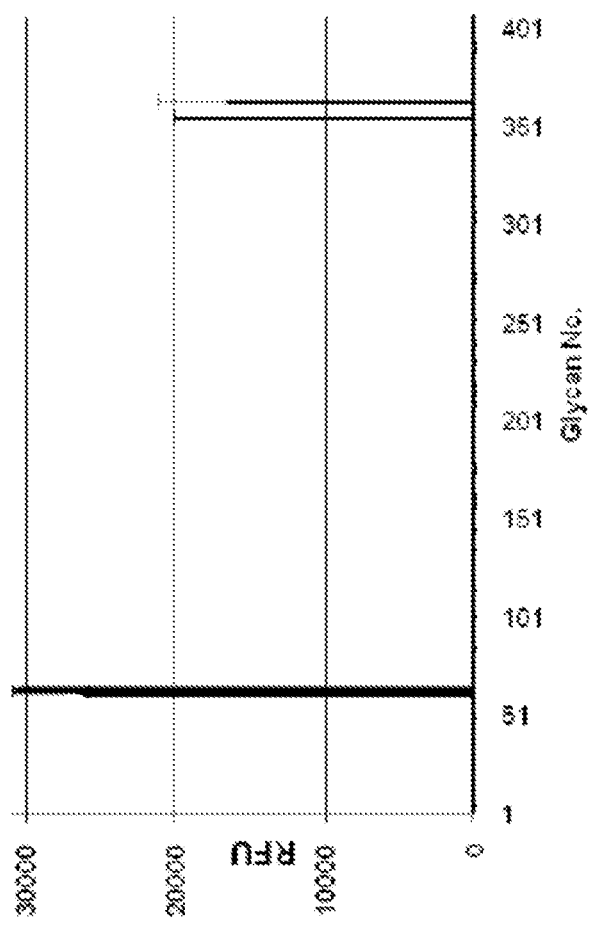
FIG. 2. Binding of 8e11 to various members of the glycan array, where y-axis indicates binding intensity expressed in relatively fluorescence units (RFU) and x-axis indicates the numerical designation of the affixed glycans. Glycan identified in Table 1.

Literature suggests that such epithelial structures are primitive cell clusters leading us to hypothesize that 8e11 is a marker of primitive epithelium. To determine the antigen that 8e11 binds, we analyzed its binding onto glycan arrays offered by the consortium for functional glycomics. On these arrays over 400 glycans are affixed and an antibody is used to probe the surface for possible ligands. 8e11 was found to specifically bind only glycans which exhibited a terminal presentation of the motif Fucα1-2Galβ1-3GlcNAcβ also known as the H type-1 antigen (FIG. 2, table 1).

TABLE 1

Table of the 6 glycans which bound 8e11 and their RFUs. Red text indicates the H type-1 motif.

| Hybridoma Clone 8e11 anti-H1 bound antigen structures | RFU |
|---|---|
| Fucα1-2Galβ1-3GlcNAcβ-Sp0 | 30710 |
| Fucα1-2Galβ1-3GlcNAcβ-Sp8 | 30490 |
| Fucα1-2Galβ1-3GlcNAcβ1-3Galβ1-4Glcβ-Sp10 | 26118 |
| Fucα1-2Galβ1-3GlcNAcβ1-3Galβ1-4Glcβ-Sp8 | 24056 |
| Fucα1 2Galβ1-3GlcNAcβ1-2Manα1-3(Fucα1-2Galβ1-3GlcNAcβ1-2Manα1-6)Manβ1-4GlcNAcβ1-4GlcNAcβ-Sp20 | 20102 |
| Fucα1-2Galβ1-3GlcNAcβ1-3(Galβ1-4(Fucα1-3)GlcNAcβ1-6)Galβ1-4Glc-Sp21 | 16528 |

The H type-1 antigen is a primitive terminal glycan capable of exhibiting O and N linkages to surface proteins and attach directly to the cell membrane via sphingolipids. This glycan is modifiable to other glycans including the blood group AB antigens. The only commercially available anti-H type-1 antigen is sold by Abcam and binds with significantly less fluorescence intensity compared to 8e11 on flow cytometry and also exhibits a different preference for presentations of the H type-1 antigen.

To test the ability of 8e11 alone to remove teratoma-forming ES cells via FACS we differentiated ES cells with RA for more than 2 weeks so that the vast majority of the culture was differentiated and not teratoma-forming. We then added undifferentiated ES cells to 1% of the final cell number. Using FACS we sorted the cells high and low in 8e11 expression. Monitoring luciferase signal, we found that the 8e11 high population rapidly formed large teratomas while 8e11 low populations formed small teratomas if at all (FIG. 1).

Using 8e11 to fractionate a culture of undifferentiated ES cells, we also found teratoma formation for both 8e11 high and low populations with only a slight increase in size in the 8e11 high population (FIG. 1). However for both assays 8e11 high and low sorted cells were found to produce teratomas as evident by the histological evidence of all three germ layers (FIG. 1). This finding led us to believe that 8e11 was insufficient by itself to deplete teratomas on its own.

Figure 3:
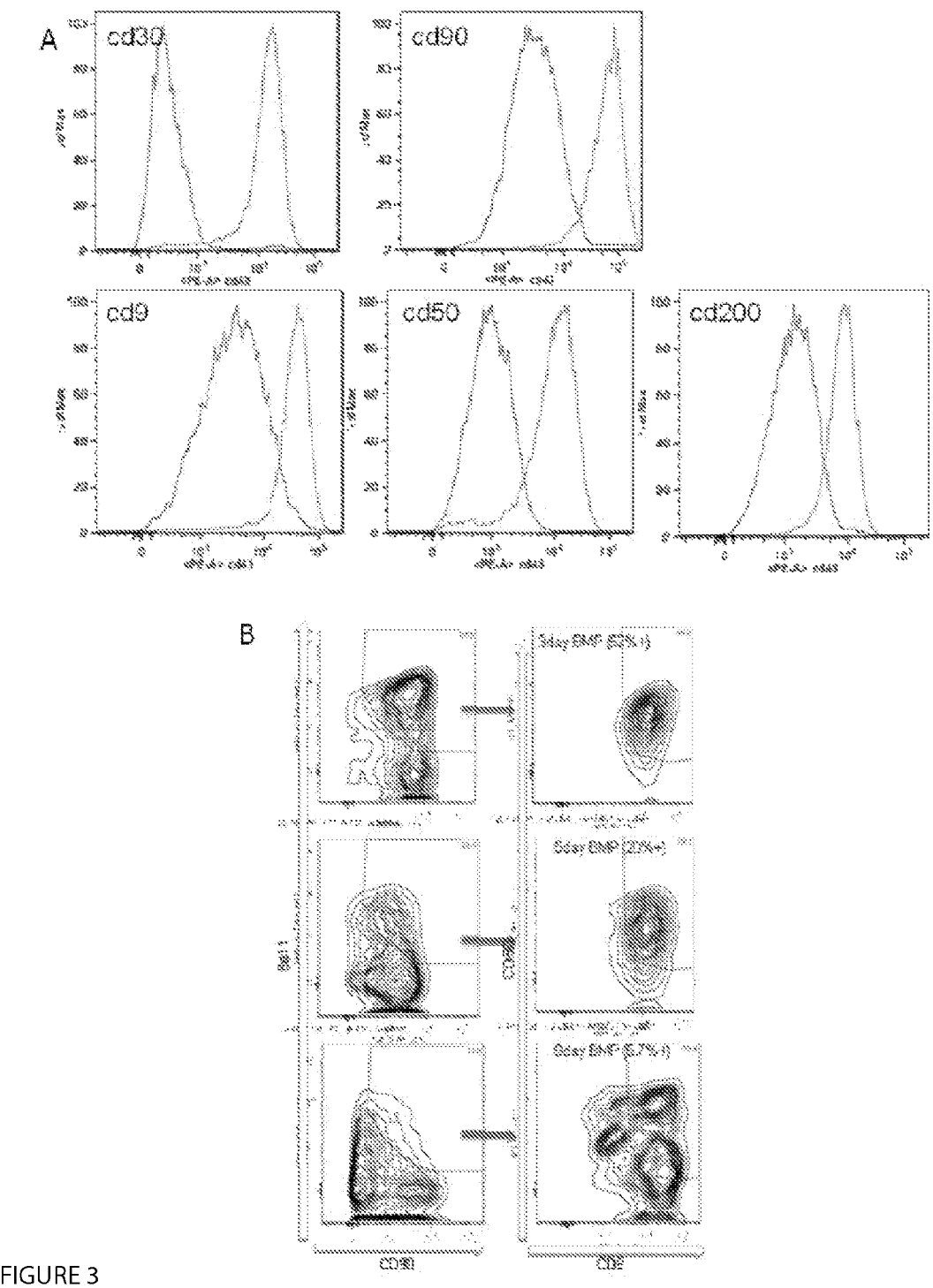
FIG. 3. Flow cytometry of undifferentiated and differentiated ES cells using additional pluripotency surface markers. A) Single color stains of five surface markers on undifferentiated (red) versus 7 day RA differentiated (blue). B) Four color stains of ES cells differentiated in BMP for 3, 5, and 9 days using the antibodies 8e11, cd9, cd50, and cd90.
Figure 4:
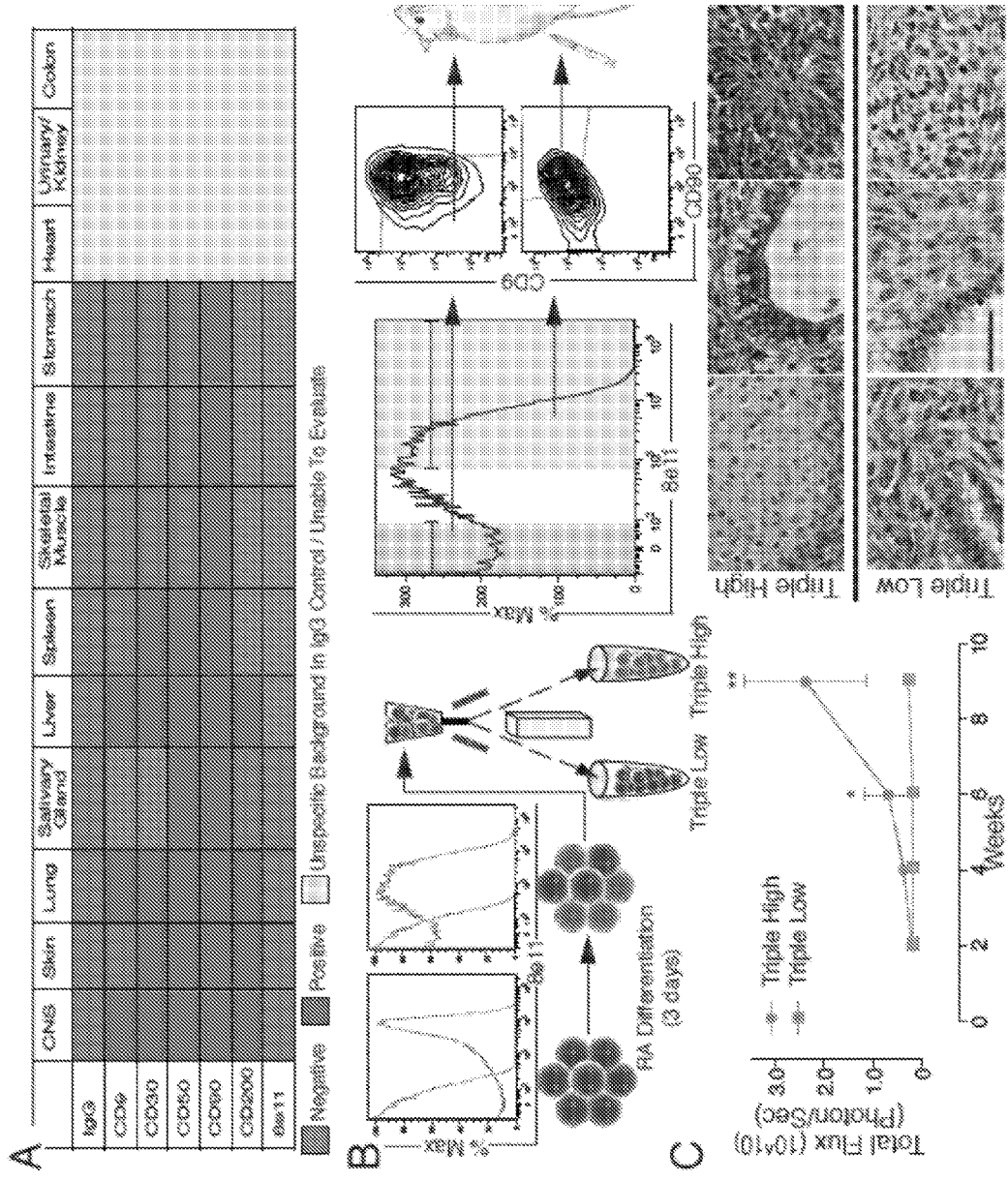
FIG. 4. PSM expression and application to remove teratoma-initiating cells. (a) Heat map representation of PSM binding to 12 human fetal tissues. Red represents >5 cells exhibiting specific staining. Yellow represents stains that were unable to be evaluated (strong igG control fluorescence), and green represents lack of specific staining. (b) Schematic illustration of 3 PSM depletion experiments: 3 day RA-treated hESCs (red circles) were sorted for 8e11, CD9, and CD90 high (triple high) and 8e11, CD9, CD90 low (triple low) and injected under kidney capsules of immunodeficient mice. Inset FACS plots present 8e11 expression and gating throughout experiment. (c) Time series luciferase signal of engrafted triple high (red) and triple low (blue) populations. Right panels are representative Hematoxylin and Eosin histological sections of tissues from the triple high and low populations. Scale bar: 100 um, (*) p-value<0.05, and (**) p-value<0.01.

To identify additional antigens that discern undifferentiated ES cells, we analyzed the binding of over 400 commercial mAbs targeting human surface molecules via flow cytometry. Over successive iterations using different differentiation conditions, we identified five additional surface markers of interest that are uniquely expressed only on undifferentiated ES/iPS cells—these five markers plus 8e11 are hereafter referred to as the pluripotency surface markers. Flow cytometry revealed that the pluripotency surface markers are concomitantly expressed at high levels in undifferentiated ES cultures, while cells differentiated in RA (FIG. 3a) or BMP exhibit marked decreases in expression. ES cells were found to concomitantly decrease expression of all four markers in the presence of BMP so that the percentage of cells expressing all four markers (i.e. the theoretical true undifferentiated ES cell) decreased from 52% at day 3 to 20% at day 5 to finally 5.7% at day 9 (FIG. 3b). We then used 3 antibodies (8e11, cd9, cd90) to costain and fractionate a culture of ES cells (similar to experiment represented in FIG. 1) and found that only the population expressing all 3 markers formed teratomas, with evidence of all 3 germ layers, while those negative for the 3 markers only formed limited growths, if at all, and these growths only exhibited histological evidence of epithelium and stroma (FIG. 4b).

We have also noticed that iPS cell cultures express the pluripotency surface markers in manners similar to that observed in the tested H9 ES cell line. We are recapitulating teratoma formation studies with iPS cells.

The clinical application of ES/iPS derived therapeutics may entail the transplantation of billions of ES/iPS derived cells into a large number of patients, many of whom will be expected to live for decades after such a procedure. As such, it is critical to develop methodologies to ensure the removal of teratome-forming cells. The pluripotency surface markers discussed here are provides a solution. The combination of these pluripotency surface markers uniquely defines the undifferentiated ES/iPS state. As such, through the application of FACS, residual teratoma-forming cells can be sorted out in a manner that can be applied to effectively "clean" any ES/iPS cell derived product before clinical application.

What is claimed is:

1. A method of depleting teratoma-forming pluripotent stem cells from a mixed cell population comprising cells differentiated from the pluripotent stem cells, the method comprising:
    contacting a mixed population of cells suspected of comprising pluripotent stem cells with an antibody that specifically binds an H type-1 antigen epitope recognized by monoclonal antibody 8e11; and
    depleting from said population those cells that bind to the antibody, to provide a differentiated cell population depleted of teratoma-forming pluripotent stem cells.

2. The method of claim 1, wherein the antibody that specifically binds an H type-1 antigen is monoclonal antibody 8e11.

3. The method of claim 1, further comprising contacting the mixed population of cells suspected of comprising pluripotent stem cells with a cocktail of antibodies specific for CD9, CD30, CD50, CD90, CD200 and H type-1 antigen; and
    depleting from said population those cells that bind to the cocktail of antibodies.

4. The method of claim 1, wherein the contacting is performed in vitro.

5. The method of claim 3, wherein the pluripotent stem cell is one or more of an induced pluripotent stem cell (iPS), embryonic stem cell and embryonic germ cell.

6. The method of claim 1 wherein the depleted population contains less than 1 in $10^9$ teratogenic pluripotent cells.

7. The method of claim 1 wherein said contacting is performed in vivo.

8. The method of claim 7, wherein the pluripotent stem cell is present.

* * * * *